(12) United States Patent
Roberts et al.

(10) Patent No.: US 7,226,792 B2
(45) Date of Patent: Jun. 5, 2007

(54) METHOD FOR SELECTING AN OPTIMAL DIET AND EXERCISE REGIMEN BASED ON LDL AND HDL SUBCLASS DETERMINATION

(75) Inventors: Amy C. Roberts, San Francisco, CA (US); David T. Shewmake, San Francisco, CA (US)

(73) Assignee: Berkeley HeartLab, Inc., Burlingame, CA (US)

( * ) Notice: Subject to any disclaimer, the term of this patent is extended or adjusted under 35 U.S.C. 154(b) by 32 days.

(21) Appl. No.: 10/854,402

(22) Filed: May 26, 2004

(65) Prior Publication Data

US 2005/0009193 A1 Jan. 13, 2005

Related U.S. Application Data

(60) Provisional application No. 60/473,715, filed on May 27, 2003.

(51) Int. Cl.
*G01N 33/92* (2006.01)

(52) U.S. Cl. .............................. 436/71; 436/63; 705/3

(58) Field of Classification Search .................. 436/71, 436/63, 95; 705/3
See application file for complete search history.

(56) References Cited

U.S. PATENT DOCUMENTS

| | | | | |
|---|---|---|---|---|
| 5,925,229 A | * | 7/1999 | Krauss et al. ................ | 204/606 |
| 6,576,471 B2 | * | 6/2003 | Otvos .......................... | 436/71 |
| 6,812,033 B2 | * | 11/2004 | Shewmake et al. ........... | 436/71 |
| 2003/0208108 A1 | * | 11/2003 | Shewmake et al. ......... | 600/300 |
| 2003/0235918 A1 | * | 12/2003 | Shewmake et al. ........... | 436/13 |

* cited by examiner

*Primary Examiner*—Maureen M. Wallenhorst
(74) *Attorney, Agent, or Firm*—McDonnell Boehnen Hulbert & Berghoff LLP

(57) ABSTRACT

The invention provides novel methods for selecting an optimal diet and exercise regimen for a patient based on the consideration of several factors, including low density lipoprotein (LDL) and high density lipoprotein (HDL) subclass levels. Furthermore, the invention provides novel methods for treating a patient with cardiovascular disease (CVD) or at risk of developing CVD through selection of an optimal diet and exercise regimen, based on the measurement of risk factors, including LDL and HDL subclass levels.

4 Claims, No Drawings

METHOD FOR SELECTING AN OPTIMAL DIET AND EXERCISE REGIMEN BASED ON LDL AND HDL SUBCLASS DETERMINATION

This application claims the benefit of U.S. Provisional Application No. 60/473,715, filed May 27, 2003.

BACKGROUND OF THE INVENTION

1. Field of the Invention

The invention relates to the fields of medicine and physiology, and especially to cardiovascular disease (CVD) treatment and prevention. In particular, the invention relates to a method for selecting an optimal diet and exercise regimen based, at least in part, on a low density lipoprotein (LDL) and high density lipoprotein (HDL) subclass (sometimes also referred to as "subfraction") determination.

2. Description of the Related Art

Cardiovascular disease (CVD), principally heart disease and stroke, is the nation's leading killer of both men and women among all racial and ethnic groups. In particular, heart disease and stroke are the first and third leading causes of death in the United States, accounting for more than 40% of all deaths. About 950,000 Americans die of heart disease or stroke each year, which amounts to one death every 33 seconds. Looking at only deaths due to heart disease or stroke, however, understates the health effects of these two conditions: about 61 million Americans live with the effects of stroke or heart disease; heart disease is a leading cause of disability among working adults; stroke alone accounts for the disability of more than 1 million Americans; and almost 6 million hospitalizations each year are due to heart disease or stroke. Moreover, the economic effects of heart disease and stroke on the U.S. health care system grows larger as the population ages. In 2001, for example, the estimated cost of CVD was $298 billion, including health care expenditures and lost productivity.

Several behavioral risk factors (e.g., obesity and physical inactivity) and preventive practices (e.g., weight loss) are associated with the development of CVD. Obesity is associated with high rates of CVD deaths, especially sudden death among men and congestive heart failure among women. The high death rate might occur largely as a consequence of the influence of obesity on blood pressure, blood lipid levels, and the onset of diabetes; however, some studies indicate that obesity is also an independent risk factor for CVD. Physical inactivity has also been shown to be a major risk factor for heart disease. Additional evidence shows an association between regular moderate-intensity physical activity and the lowering of several other risk factors for CVD, including blood lipid levels, resting blood pressure among persons with borderline hypertension, body composition and overweight and glucose tolerance and insulin sensitivity. Weight control, meanwhile, is a first step in the control of mild hypertension hyperlipidemia, and impaired glucose tolerance and might eliminate the necessity of lifelong drug therapy for these conditions. Efforts to control weight generally have not been effective; however, researchers have demonstrated recently the effectiveness of combined programs of behavior modification of diet and exercise (Jeffery R W (1995) Obesity Research 3(suppl.): 283s–288s; Brownell K D (1986) Annu Rev Public Health 7:521). Moreover, therapeutic approaches to weight control that emphasize increased physical activity have other benefits in addition to increasing caloric expenditure (Powell K E et al. (1987) Annu Rev Public Health 8:253).

Although it has been known for some time that an appropriate diet and exercise regimen may be useful in the prevention and treatment of CVD, there remains a need for methods of selecting an optimal diet and exercise regimen that may be used in the treatment and prevention of CVD. In particular, there is a need in the art for methods for selecting an optimal diet and exercise regimen based on the evaluation of risk factors such as LDL and HDL subclass levels. The present invention provides such methods.

BRIEF SUMMARY OF THE INVENTION

The invention relates to methods for selecting an optimal diet and exercise regimen for a patient and to methods for treating a patient comprising selecting an optimal diet and exercise regimen.

In one embodiment, the invention provides a method for selecting an optimal diet and exercise regimen for a patient, comprising considering one or more LDL or HDL subclass levels in the patient; and selecting a diet and exercise regimen based on the LDL or HDL subclass level considered.

In a further embodiment, the invention provides a method for selecting an optimal diet and exercise regimen for a patient, comprising considering the patient's age, gender, height, and weight; and considering one or more factors selected from the group consisting of: LDL IIIa+IIIb, HDL 2(b), HDL-C, LDL-C, APO B, glucose, insulin, triglycerides, homocysteine, and Lp(a) levels; and APO E genotype; and selecting a diet and exercise regimen based on the above considerations.

In yet a further embodiment, the invention provides a method for treating a patient, comprising selecting a diet and exercise regimen according to one of the methods described above; prescribing the selected diet and exercise regimen to the patient; and monitoring one or more LDL or HDL subclass levels in the patient.

DETAILED DESCRIPTION OF THE INVENTION

The invention comprises methods for selecting an optimal diet and exercise regimen for a patient based on the consideration of several factors. Such factors include LDL and HDL subclass levels—for example, LDL IIIa+IIIb and HDL 2(b). LDL and HDL subclass levels may be expressed in quantitative terms, such as, for example, mg/dL. Additional factors include the patient's age, gender, height, and weight. Still further factors include additional biochemical levels measured in a sample taken from the patient, including HDL-C, LDL-C, APO B, glucose, insulin, triglycerides, homocysteine, and Lp(a) levels, and APO E genotype. One or more of the above factors may be considered in selecting an optimal diet and exercise regimen according to the methods of the invention. Moreover, the invention comprises methods for treating a patient comprising selecting an optimal diet and exercise regimen according to the method of selecting an optimal diet and exercise regimen of the invention.

LDL and HDL subclasses may be determined by gradient gel electrophoresis (GGE), NMR, ultracentrifugation, or ion mobility analysis. One example of such a GGE method is the Berkeley HeartLab $S_3GGE$™ process, which is one of the most accurate methods of LDL and HDL subclass determination. See, for example, U.S. Pat. No. 5,925,229, entitled "Low Density Lipoprotein Fraction Assay for Cardiac Disease Risk." In addition to the proprietary LDL and HDL S₃GGE™ tests, Berkeley HeartLab provides several additional tests and panels that identify other metabolic disorders that may increase risk for the development and manifestation of cardiovascular disease (CVD). The Berkeley HeartLab tests provide the physician with the most comprehensive assessment of a patient's inherited cardiovascular metabolic disorders.

Berkeley HeartLab has additionally developed a proprietary database containing information on over 100,000 CVD patients, including quantitative information regarding LDL and HDL subclass levels. The database contains LDL and HDL subclass data expressed in terms of mg/dL. The information contained in the database and methods associated with its use may be used in conjunction with the present invention. The database and associated methods are described in U.S. patent application Ser. No. 10/412,838, entitled "A Method for Identifying At Risk Cardiovascular Disease Patients," filed Apr. 12, 2003, which is hereby incorporated by reference in its entirety.

The invention may further be used in conjunction with the health care management system described in U.S. patent application Ser. No. 09/534,946, entitled "Cardiovascular Healthcare Management System and Method," filed Mar. 24, 2000, which is hereby incorporated by reference in its entirety. Furthermore, Heart Disease Breakthrough, by Thomas Yannios, M.D. John Wiley & Son, Inc., New York, 1999, which is hereby incorporated by reference in its entirety, discusses management of heart disease and the role of HDL and LDL subclasses therein and may also be useful to those practicing the methods of the invention.

Berkeley HeartLab test results provide the physician with the ability to develop baseline determination of a patient's CVD risk profile. This determination is the first step in changing the management of the patient's disease. The accurate determination of the patient's cardiovascular risk factors will guide the development of a personalized treatment plan. The follow-up use of Berkeley HeartLab testing services offers the physician the ability to monitor the patient's progress relative to the individual treatment plan developed. Based on the diagnostic outcome, an individual's treatment plan is modified according to the results of follow-up testing.

Low HDL 2(b) (e.g., when HDL 2(b) is 10% or less of HDL cholesterol for males; 20% or less for females) is a high priority risk factor for both mortality (Barbagallo C M et al. (1998) Gerontology 44:106–10) and morbidity (Lamarche B et al. (2001) Can J Cardiol 17:859–65). Very low (20%) fat and not-so-low (25%) fat diets often worsen this independent cardiovascular risk factor (Williams P T and Krauss R M (1999) Am J Clin Nutr 70:949–50; Williams P T et al. (1995) Am J Clin Nutr 61:1234–40). Therefore, a diet moderate in fat content, consisting of 30–35% of total calories, is recommended. However, it is very important that recommended fat intake be primarily from plant or monounsaturated sources and fish. Animal protein (but not fish) is very high in saturated fat and should be consumed in moderation. Diet should be high in soluble fiber (oat bran, fruits, vegetables), whole grains/starches, fish and plant (soy) proteins and low in processed grains/starches and animal proteins. A smaller amount of food at more frequent intervals is also recommended as increasing meal frequency (but not total caloric intake) decreases cardiovascular risk (Arnold L M et al. (1993) Am J Clin Nutr 57:446–51). Caloric content of diet is very important as restriction of calorie content alone may lead to increases in HDL 2(b). Alcohol should be avoided.

APO E 2/2 and 2/3 individuals may be sensitive to simple sugars and often have a significant elevation in TG due in part to delayed catabolism of chylomicron and VLDL remnants (Krauss R M (2001) J Nutr 131:340S–3S). This population has a better outcome when diet is higher in fat rather than sugar. Dietary fiber has a very good cholesterol lowering effect in these individuals. Therefore, a diet moderate in fat content, consisting of 30–35% of total calories, is recommended. Diet should be particularly high in soluble fiber (oat bran, fruits, vegetables), whole grains/starches, fish and plant (soy) proteins and low in processed grains/starches. Consuming fish twice each week or supplementing with fish oils or flax seeds has been shown to lower postprandial TG's and possibly increase lipoprotein lipase activity in this population. A smaller amount of food at more frequent intervals is also recommended as increasing meal frequency (but not total caloric intake) decreases cardiovascular risk. Individuals with this phenotype are very responsive to exercise for improving cardiovascular risk levels. A very small percentage of homozygous APO E2 individuals (<1%) are at risk of developing Type III hyperlipidemia. If the patient does not respond to recommended dietary intervention, the approach should be modified. Note that there are more diabetic patients with the E2 allele, so screening for diabetes might be warranted if responsiveness to dietary intervention is not effective.

Diets lower in fat (less than 25%) are not recommended for individuals with high triglycerides (e.g., 150–199 mg/dL) (Hudgins L C (2000) Proc Soc Exp Biol Med 225:178–83). Furthermore, diets high in simple sugars and highly processed foods have proven disadvantageous in this patient population (Xue C Y et al. (2001) Int J Obes Relat Metab Disord 25:434–8). A diet ranging in fat content from 30–35% of total daily calories is recommended (Kris-Etherton P M et al. (2000) J Cardiovasc Risk 7:333–7). Food choices should include fats from monounsaturated fats (15% of total calories) and omega-3's (fish or fish oil supplementation equivalent to 3 g/day) (Durrington P N et al. (2001) Heart 85:544–8) with a limited quantity of saturated/trans fats (less than 7% of total calories). For this population sugar is definitely worse than fat and choosing low glycemic index foods tend to improve both triglyceride and HDL profiles (Pelkman C L (2001) Curr Atheroscler Rep 3:456–61). Diet should be high in soluble fiber (oat bran, vegetables), whole grains/starches, fish and plant (soy) proteins and low in processed grains/starches, fruits and animal proteins. A smaller amount of food at more frequent intervals is also recommended as increasing meal frequency (but not total caloric intake) decreases cardiovascular risk. The amount of simple/processed sugars should be limited, as should fruit and fruit juice. Alcohol should be avoided. Refer to "low", "moderate" and "high" food from the Glycemic Index Table. Fish should be consumed twice each week or diet should be supplemented with flax seeds or fish oils. Close attention should be paid to caloric intake.

The moderate (35%) fat diet with only "healthy" foods is designed to help improve LDL IIIa+IIIb levels (Nicolosi R J et al. (2001) J Am Coll Nutr 20(5 Suppl):421S–427S; discussion 440S–442S). Diet should be moderate in fat content, consisting of 30–35% of total calories. The type of dietary fat should be primarily from monounsaturated fats (15% of total calories) with a limited quantity of saturated/trans fats (less than 7% of total calories). More extreme reduction in fat intake (e.g., to less than 25% of total calories) offers little further advantage with potentially undesirable effects in patients with high cholesterol (Knopp R H et al. (1997) JAMA 278:1509–15). Calorie content of diet must be appropriate for weight maintenance or weight loss depending on goal weight or % body fat (de Man F H et al. (1999) Eur J Clin Nutr 53:413–8). Diet should be high in soluble fiber (oat bran, fruits, vegetables), whole grains/starches, fish and plant (soy) proteins and low in processed grains/starches and animal proteins. Diet should include fish at least twice each week or should be supplemented with fish oils or flax seeds. A smaller amount of food at more frequent intervals is also recommended as increasing meal frequency (but not total caloric intake) decreases cardiovascular risk. Alcohol should be avoided.

Patients with elevated glucose levels (e.g., 110 mg/dL or higher) should be monitored closely in order to prevent further disease progression and additive complications such as Type-2 diabetes (Packard C et al. (2000) Int J Cardiol 74 Suppl 1:S17–22). It is very likely that traditional treatment of these patients actually worsened their condition (Reaven G (2001) Current Treatment Options in Cardiovascular Medicine 3:323–332). Very low (20%) fat diets and diets high in simple or processed carbohydrates are not recommended (Superko H R (2001) Current Treatment Options in Cardiovascular Medicine 2:173–187). Instead, diets consisting of 30–35% fat should not further complicate their metabolic condition. More extreme reduction in fat intake (e.g., to less than 25% of total calories) offers little further advantage with potentially undesirable effects in patients with combined hyperlipidemic profile. Calorie content of preventive diet must be appropriate for weight maintenance or weight loss depending on calculated goal weight or % body fat. Diet should be high in soluble fiber (oat bran, fruits, vegetables), whole grains/starches, fish and plant (soy) proteins and low in processed grains/starches (no sucrose or fructose) and animal proteins. Supplementation with Omega-3 fatty acids (fish oil, flax seeds) is suggested (Minihane A M et al. (2000) Arterioscler Thromb Vasc Biol 20:1990–7). A smaller amount of food at more frequent intervals is also recommended as increasing meal frequency (but not total caloric intake) decreases cardiovascular risk. Simple sugars should be avoided. Diet should include fish at least twice each week or should be supplemented with fish oils or flax seeds. Low glycemic index foods should be chosen. Alcohol should be avoided. Careful control of caloric intake is suggested. Patients should refer to "low", "moderate" and "high" food from the Glycemic Index Table.

Patients with elevated insulin levels (e.g., 12 μU/ml or higher) should be monitored closely in order to prevent further disease progression and additive complications such as Type-2 diabetes. It is very likely that traditional treatment of these patients actually worsened their condition. Very low (20%) fat diets and diets high in simple or processed carbohydrates are not recommended. Instead, diets consisting of 30–35% fat should not further complicate their metabolic condition. More extreme reduction in fat intake (e.g., to less than 25% of total calories) offers little further advantage with potentially undesirable effects in patients with combined hyperlipidemic profile. Calorie content of preventive diet must be appropriate for weight maintenance or weight loss depending on calculated goal weight or % body fat. Diet should be high in soluble fiber (oat bran, fruits, vegetables), whole grains/starches, fish and plant (soy) proteins and low in processed grains/starches (no sucrose or fructose) and animal proteins. Supplementation with Omega-3 fatty acids (fish oil, flax seed) is suggested. A smaller amount of food at more frequent intervals is also recommended as increasing meal frequency (but not total caloric intake) decreases cardiovascular risk. Simple sugars should be avoided. Diet should include fish at least twice each week or should be supplemented with fish oils or flax seeds. Low glycemic index foods should be chosen. Alcohol should be avoided. Careful control of caloric intake is suggested. Patients should refer to "low", "moderate" and "high" food from the Glycemic Index Table.

There is ample evidence to suggest that an elevated triglyceride level (e.g., 200–999 mg/dL) is an independent cardiovascular risk factor (Miller M (2000) Am Heart J 140:232–40). However, this risk factor is usually accompanied by a cascade of other lipid abnormalities that deserve aggressive treatment (Li J et al. (2000) Clin Chem Lab Med 38:1263–70). For this reason treatment strategy is usually prioritized when elevated triglyceride values are in combination with other risk levels. Usually it is appropriate to initially improve LDL subclass distribution and LDL-C levels and to raise HDL 2(b) and HDL-C values. However, when triglycerides become higher, it becomes necessary to approach the treatment of this risk factor more aggressively. Weight loss and exercise are important in order to increase lipoprotein-lipase activity and dietary modification including caloric restriction is also an essential component of aggressive therapy. Diets lower in fat (less than 25%) are not recommended for individuals with elevated triglycerides. Furthermore, diets high in simple sugars and highly processed foods have proven disadvantageous in this patient population. A diet ranging in fat content from 30–35% of total daily calories is recommended. Food choices should include fats from monounsaturated fats (15% of total calories) and omega-3's (fish or fish oil supplementation equivalent to 3 g/day) with a limited quantity of saturated/trans fats (less than 7% of total calories). For this population sugar is definitely worse than fat and choosing low glycemic index foods tend to improve both triglyceride and HDL profiles. Diet should be high in soluble fiber (oat bran, vegetables), whole grains/starches, fish and plant (soy) proteins and low in processed grains/starches, fruits and animal proteins. A smaller amount of food at more frequent intervals is also recommended as increasing meal frequency (but not total caloric intake) decreases cardiovascular risk. Simple/processed sugars and fruit should be limited, while fruit juice and alcohol should be avoided. Refer to "low", "moderate" and "high" food from the Glycemic Index Table. Diet should include fish at least twice each week or should be supplemented with fish oils or flax seeds. Close attention should be paid to caloric intake.

The population of patients with diabetes mellitus represents a very large percentage of patients with high cardiovascular risk (Superko H R (1999) Curr Atheroscler Rep 1:50–7). It is very likely that traditional treatment of these patients actually worsened their condition. Very low (20%) fat diets and diets high in simple or processed carbohydrates are not recommended. Instead diets consisting of 30–35% fat should not further complicate their metabolic condition. More extreme reduction in fat intake (e.g., to less than 25% of total calories) offers little further advantage with potentially undesirable effects in patients with combined hyperlipidemic profile. Calorie content of preventive diet must be appropriate for weight maintenance or weight loss depending on calculated goal weight or % body fat. Diet should be high in soluble fiber (oat bran, fruits, vegetables), whole grains/starches, fish and plant (soy) proteins and low in processed grains/starches (no sucrose or fructose) and animal proteins. Supplementation with Omega-3 fatty acids (fish oil, flax seed) is suggested. A smaller amount of food at more frequent intervals is also recommended as increasing meal frequency (but not total caloric intake) decreases cardiovascular risk. Simple sugars should be avoided. Diet should include fish at least twice each week or should be supplemented with fish oils or flax seeds. Low glycemic index foods should be chosen. Alcohol should be avoided. Smaller meals and more frequent feeding are recommended. Careful control of caloric intake is suggested. Patients should refer to "low", "moderate" and "high" food from the Glycemic Index Table.

Daily fat intake for basic prevention of cardiovascular disease should be low—e.g., consisting of 25–30% of daily total calories. The type of dietary fat should be primarily from monounsaturated fats (15–20% of total calories) with a limited quantity of saturated/trans fats (less than 7% of total calories). More extreme reduction in fat intake (e.g., to less than 25% of total calories) offers little further advantage with potentially undesirable effects. Calorie content of preventive diet must be appropriate for weight maintenance or weight loss depending on calculated goal weight or % body fat. Diet should be high in soluble fiber (oat bran, fruits, vegetables), whole grains/starches, fish and plant (soy) proteins and low in processed grains/starches and animal proteins. A smaller amount of food at more frequent intervals is also recommended as increasing meal frequency (but not total caloric intake) decreases cardiovascular risk.

The not-so-low (25%) fat diet is a good prevention diet and is also appropriate for maintaining LDL IIIa+IIIb levels. Daily fat intake should consist of 25–30% of daily total calories. The type of dietary fat should be primarily from monounsaturated fats (15% of total calories) with a limited quantity of saturated/trans fats (less than 7% of total calories). More extreme reduction in fat intake (e.g., to less than 25% of total calories) offers little further advantage with potentially undesirable effects in patients with high cholesterol. Calorie content of diet must be appropriate for weight maintenance or weight loss depending on goal weight or % body fat. Diet should be high in soluble fiber (oat bran, fruits, vegetables), whole grains/starches, fish and plant (soy) proteins and low in processed grains/starches and animal proteins. A smaller amount of food at more frequent intervals is also recommended as increasing meal frequency (but not total caloric intake) decreases cardiovascular risk. Alcohol should be avoided.

A diet ranging in fat content from 25–30% of total daily calories has proven helpful in improving LDL-C. The type of dietary fat should be primarily from monounsaturated fats (15% of total calories) with a limited quantity of saturated/trans fats (less than 7% of total calories). Calorie content of diet must be appropriate for weight maintenance or weight loss depending on calculated goal weight or % body fat. Diet should be high in soluble fiber (oat bran, fruits, vegetables), whole grains/starches, fish and plant (soy) proteins and low in processed grains/starches and animal proteins. A smaller amount of food at more frequent intervals is also recommended as increasing meal frequency (but not total caloric intake) decreases cardiovascular risk. Alcohol should be avoided.

Individuals who are homozygous for the APO E3 allele (and APO E 2/4 due to similarity in responsiveness) should follow a basic preventive diet. Therefore, daily fat intake for prevention of cardiovascular disease should be low, consisting of 25–30% of daily total calories. The type of dietary fat should be primarily from monounsaturated fats (15–20% of total calories) with a limited quantity of saturated/trans fats (less than 7% of total calories). More extreme reduction in fat intake (e.g., to less than 25% of total calories) offers little further advantage with potentially undesirable effects. Calorie content of preventive diet must be appropriate for weight maintenance or weight loss depending on calculated goal weight or % body fat. Diet should be high in soluble fiber (oat bran, fruits, vegetables), whole grains/starches, fish and plant (soy) proteins and low in processed grains/starches and animal proteins. A smaller amount of food at more frequent intervals is also recommended as increasing meal frequency (but not total caloric intake) decreases cardiovascular risk.

There are no established dietary measures for reducing elevated blood levels of Lp(a) (Durstine J L et al. (2001) Med Sci Sports Exerc 33:1511–6). However, dietary antioxidants may inhibit the oxidative processes that intensify the contribution of Lp(a) to atherosclerosis. A diet that is high in antioxidant foods or vitamins may help to prevent the oxidation of Lp(a) and other lipoproteins. Daily fat intake for prevention of cardiovascular disease should be low, consisting of 25–30% of daily total calories. The type of dietary fat should be primarily from monounsaturated fats (15–20% of total calories) (Rajaram S et al. (2001) J Nutr 131:2275–9) with a limited quantity of saturated/trans fats (less than 7% of total calories). More extreme reduction in fat intake (e.g., to less than 25% of total calories) offers little further advantage with potentially undesirable effects. Calorie content of preventive diet must be appropriate for weight maintenance or weight loss depending on calculated goal weight or % body fat. Diet should be high in soluble fiber (oat bran, fruits, vegetables), whole grains/starches, fish and plant (soy) proteins and low in processed grains/starches and animal proteins. A smaller amount of food at more frequent intervals is also recommended as increasing meal frequency (but not total caloric intake) decreases cardiovascular risk. Refer to Tables for Beta-carotene in Fruits and Vegetables and Vitamin E Content of foods.

Homocysteinemia, or a high level of homocysteine in the blood (e.g., 14 μmol/L or higher), is found in 20% of CAD patients and 30% of patients with peripheral vascular disease (Ward M (2001) Int J Vitam Nutr Res 71:173–8). One way to help reduce the homocysteine level is to supplement the diet with two B vitamins, folic acid and vitamin B6 (Bayes B et al. (2001) Nephrol Dial Transplant 16:2172–5; de Bree A et al. (2001) Am J Epidemiol 154:150–4; Herrmann W et al. (2001) Clin Chem 47:1094–101; Ward M et al. (2001) Int J Vitam Nutr Res 71:82–6). As much as a 50% reduction in homocysteine levels has been shown by B vitamin supplementation. It may also be beneficial to avoid excess dietary intake of methionine, which the body changes to homocysteine (Dobiasova M et al. (2001) Physiol Res 50:1–8). This precursor of homocysteine tends to be abundant in foods that are high in protein such as meat, fish, poultry, eggs, and dairy products. Animal products should be avoided. The methionine content of foods should be noted and those that are ranked as high (in bold on the Methionine table) should be avoided. Vegetarian entrees should be chosen whenever possible. Soy protein is low in methionine, and is an excellent source of protein. Soy milk fortified with calcium should be chosen in place of regular milk whenever possible. Foods high in B vitamins should be consumed. B vitamin supplementation should be considered. See Tables for B Vitamin (Folic Acid and B6) and Methionine content of common foods.

Borderline high LDL IIIa+IIIb (e.g., when LDL IIIa+IIIb is 16–34% of LDL-C cholesterol) individuals are usually very responsive to appropriate lifestyle interventions. Diet should be moderate in fat content, consisting of 30–35% of total calories. More extreme reduction in fat intake (e.g., to less than 25% of total calories) offers little further advantage with potentially undesirable effects in patients with high cholesterol. Animal protein (but not fish) is very high in saturated fat and should be consumed in moderation. Diet should be high in soluble fiber (oat bran, fruits, vegetables), whole grains/starches, fish and plant (soy) proteins and low in processed grains/starches and animal proteins. A smaller amount of food at more frequent intervals is also recommended as increasing meal frequency (but not total caloric intake) decreases cardiovascular risk. Diet should include fish twice each week or be supplemented with fish oils or flax seeds. Alcohol should be avoided.

A diet ranging in fat content from 25–30% of total daily calories has proven helpful in improving LDL-C levels. The type of dietary fat should be primarily from monounsaturated fats (15–20% of total calories) with a limited quantity of saturated/trans fats (less than 7% of total calories). Calorie content of diet must be appropriate for weight maintenance or weight loss depending on calculated goal weight or % body fat. Diet should be high in soluble fiber (oat bran, fruits, vegetables), whole grains/starches, fish and plant (soy) proteins and low in processed grains/starches and animal proteins. A smaller amount of food at more frequent intervals is also recommended as increasing meal frequency (but not total caloric intake) decreases cardiovascular risk. Alcohol should be avoided.

A diet ranging in fat content from 25–30% of total daily calories is recommended to improve LDL-cholesterol as defined by APO B (e.g., APO B level of 110 mg/dL or higher). The type of dietary fat should be primarily from monounsaturated fats (15–20% of total calories) with a limited quantity of saturated/trans fats (less than 7% of total calories). Calorie content of diet must be appropriate for weight maintenance or weight loss depending on calculated goal weight or % body fat. Diet should be high in soluble fiber (oat bran, fruits, vegetables), whole grains/starches, fish and plant (soy) proteins and low in processed grains/starches and animal proteins. A smaller amount of food at more frequent intervals is also recommended as increasing meal frequency (but not total caloric intake) decreases cardiovascular risk. Alcohol should be avoided.

Patients with extremely high levels of triglycerides (e.g., 1000 mg/dL or higher) are at high risk for developing pancreatitis (Hoffmann M M et al. (2000) J Clin Endocrinol Metab 85:4795–8), therefore, diet must be very low in fat (Parks E J (2001) J Nutr 131:2772S–2774S). Caloric restriction, weight loss and exercise are essential. Calorie content of diet must be restricted. Simple and highly processed sugars should be avoided. Low glycemic index foods should replace high glycemic index foods. Diet should be high in soluble fiber (oat bran, vegetables), whole grains/starches, fish and plant (soy) proteins. Processed grains/starches and animal proteins should be avoided. Supplementation of Omega-3's (3 grams/day) or daily fish consumption is recommended. Large meals should be replaced by smaller more frequent feedings. Refined carbohydrates should be avoided. Low glycemic index foods should be chosen. Alcohol is absolutely prohibited.

Individuals with at least one APO E4 allele (i.e., APO E 4/4 or 3/4, but excluding APO E 2/4) are most responsive to dietary intervention and are particularly sensitive to fat intake. A diet very low in fat (less than 20%) is recommended for this reason. It is very important for this population to consume a diet very low in saturated fats and dietary cholesterol. Animal products should be avoided. Choose vegetarian entrees whenever possible. Soy protein is an excellent source of protein. Soy milk fortified with calcium rather than regular milk should be chosen whenever possible. Alcohol is strictly prohibited as it has been shown to raise LDL cholesterol significantly in this population.

Elevated LDL-C (e.g., 160 mg/dL or higher) requires aggressive dietary intervention. A very low (less than 20%) fat diet is recommended. Diet must be low in saturated/trans fats and dietary cholesterol. Animal products should be avoided. Vegetarian entrees should be chosen whenever possible. Soy protein is an excellent source of protein. Soymilk fortified with calcium should be chosen. Diet should be high in soluble fiber (oat bran, fruit vegetables), whole grains/starches, fish and plant (soy) proteins. Alcohol should be avoided. Caloric restriction may be warranted.

The following examples are presented for illustrative purposes only and are not intended, nor should they be construed, as limiting the invention in any way. Those skilled in the art will recognize that variations on the following can be made without exceeding the spirit or scope of the invention.

EXAMPLE 1

Moderate (35%) Fat Diet

When values are independent, or not in combination with other risk factors that might modify dietary recommendation, the moderate (35%) fat diet with "healthy" and "not-as-healthy" foods is recommended for any of the following:

a) HDL 2(b)≦10% of HDL cholesterol (male); ≦20% (female);
b) APO E 2/2 or 2/3 (genotype); or
c) Triglycerides 150–199 (mg/dL).

When values are independent, or not in combination with other risk factors that might modify dietary recommendation, the moderate (35%) fat diet with only "healthy" foods is recommended for any of the following:

a) LDL IIIa+IIIb≧35% of LDL-C cholesterol;
b) Glucose≧110 (mg/dL);
c) Insulin≧12 (µU/ml);
d) Triglycerides 200–999 (mg/dL); or
e) Diabetes Mellitus.

A representative moderate (35%) fat, 2000 calorie diet for a single day is the following:

Breakfast: Apple Spiced Oatmeal (½ c oatmeal; 1 diced apple; 8 oz vanilla soy or skim milk; ground cinnamon, nutmeg, ginger and allspice; 2 T raisins).

Morning snack: 1 carrot; 5–10 jicama sticks; ⅓ c hummus.

Lunch: Stuffed Pita: 1 whole wheat pita; ½ baby spinach leaves. Mix together: 3 oz canned tuna; 1 tsp mayonnaise; 2 T diced onion; 2 T diced celery; 2 T diced tomato.

Afternoon snack: ¼ c BHL Snack Mix (½ c each, unsalted, without oil: pumpkin seeds, almonds, walnuts, soy nuts; ½ c any of the following: diced dried apricots, diced dried figs, raisins and/or cranberries; 1 c Oat Bran Cereal Squares or Oat Bran O's).

Dinner: 1½ c spinach; 2 T olive oil & vinegar; 2 T pumpkin seeds; Black Bean Ravioli (commercial frozen ravioli) topped with marinara sauce; 2 T grated parmesan cheese.

Evening snack/dessert: 1¼ c strawberries; 4 oz vanilla yogurt; 1 T ground flax seed.

The representative moderate (35%) fat, 2000 calorie diet for a single day comprises the following: 250 g carbohydrate; 75 g protein; 78 g fat w/<11 g from saturated/trans fats.

The representative moderate (35%) fat, 2000 calorie diet for a single day comprises the following point values: 7 points grain/starch; 5 points vegetable; 4 points fruit; 2 points (healthy or not-as-healthy) dairy; 4 points (healthy) protein; 1 points (not-as-healthy) protein; 12 points chosen mostly from (healthy) fat group; 2 points sweets/alcohol. This adds up to a daily total of 37 points.

EXAMPLE 2

Not-So-Low (25%) Fat Diet

When values are independent, or not in combination with other risk factors that might modify dietary recommendation, the not-so-low (25%) fat with "healthy" and "not-as-healthy" foods is recommended for any of the following:
 a) basic prevention of cardiovascular disease;
 b) LDL IIIa+IIIb≦15% of LDL-C cholesterol;
 c) LDL-C 100–129 (mg/dL);
 d) APO E 3/3 or 2/4 (genotype);
 e) Lp(a)≧20 (mg/dL); or
 f) Homocysteine≧14 (µmol/l).

When values are independent, or not in combination with other risk factors that might modify dietary recommendation, the not-so-low fat (25%) fat diet with only "healthy" foods is recommended for any of the following:
 a) LDL IIIa+IIIb 16–34% of LDL-C cholesterol;
 b) LDL-C 130–159 (mg/dL); or
 c) APO B≧110 (mg/dL).

A representative not-so-low (25%) fat, 2000 calorie diet for a single day is the following:

Breakfast: 2 c Oatbran flakes; 8 oz skim or soy milk; 1¼ c strawberries; 2 T ground flax seeds.

Morning snack: Smoothie: 8 oz soy or skim milk blended with 1 banana, 1 T honey.

Lunch: 2 c BHL Chili (15 oz can Chili Beans (kidney, black, pinto); 8 oz stewed tomatoes; 1 T minced onion; 2 T chili seasoning; ¼ c water); 6 oz nonfat yogurt; fresh cilantro; 1 whole grain roll. Salad: 2 c mixed greens; 1 c chopped carrots, broccoli, onions, peppers; 3 egg whites; 1 T pumpkin seeds; 2 T olive oil & balsamic vinegar.

Afternoon snack: 1 English muffin; 2 oz low-fat cheese; 2 T diced tomatoes.

Dinner: BHL Greens (8 c greens (kale, collards, spinach); 2 tsp olive oil; 3 cloves minced garlic; 2 T tamari or light soy sauce; 2 tsp grated fresh ginger; 2 T water; 2 tsp lemon juice or ½ lemon; red pepper flakes); 6 oz halibut with salsa; ½ acorn squash; 1 tsp non-hydrogenated margarine; 1 c wild rice; 4 walnuts.

Evening snack/dessert: 8 oz nonfat plain yogurt; 1 c berries; 1 small banana.

The representative not-so-low (25%) fat, 2000 calorie diet for a single day comprises the following: 275 g carbohydrate; 100 g protein; 55 g fat w/<11 g from saturated/trans fats.

The representative not-so-low (25%) fat, 2000 calorie diet for a single day comprises the following point values: 9 points grain/starch; 5 points vegetable; 4 points fruit; 3 points dairy; 6 points (healthy) protein; 8 points mostly (healthy) fat; 1 point sweets/alcohol. This adds up to a daily total of 36 points.

EXAMPLE 3

Very Low (20%) Fat Diet

When values are independent, or not in combination with other risk factors that might modify dietary recommendation, the very low (20%) fat diet with only "healthy" foods is recommended for any of the following:
 a) Triglycerides≧1000 (mg/dL);
 b) APO E 4/4 or 3/4 (genotype); or
 c) LDL-C≧160 (mg/dL).

A representative very low (20%) fat, 2000 calorie diet for a single day is the following:

Breakfast: 1½ c oat bran flakes; 6 oz skim or soy milk.

Morning snack: 8 oz soy or skim milk.

Lunch: 1½ c BHL Chili (see Example 2 for recipe); 6 oz nonfat yogurt; fresh cilantro; 1 whole grain roll. Salad: 2 c mixed greens; 1 c chopped carrots, broccoli, onions, peppers; 2 egg whites; 1 T pumpkin seeds; 2 T olive oil; 2 T balsamic vinegar.

Afternoon snack: 1 English muffin; 1 oz low-fat cheese; 2 T diced tomatoes.

Dinner: 2 BHL Greens (see Example 2 for recipe); 6 oz halibut with salsa; ½ acorn squash; ⅔ c wild rice; 1 tsp non-hydrogenated margarine with 1 T brown sugar and cinnamon.

Evening snack/dessert: 4 oz nonfat plain yogurt; 1 c berries.

The representative very low (20%) fat, 2000 calorie diet for a single day comprises the following: 250 g carbohydrate; 75 g protein; 78 g fat w/<11 g from saturated/trans fats.

The representative very low (20%) fat, 2000 calorie diet for a single day comprises the following point values: 9 points grain/starch; 6 points vegetable; 1 point fruit; 3 points (healthy or not-as-healthy) dairy; 9 points (healthy) protein; 5 points chosen mostly from (healthy) fat group. This adds up to a daily total of 33 points.

EXAMPLE 4

"Food as Points" System

The Berkeley HeartLab "Food as Points" system is based on the food exchange system developed by the American Dietetic Association and the American Diabetes Association in cooperation with the US Public Health Service. This system categorizes foods into major food groups, subcategorizes these foods by nutrient or fat content, and lists foods under each category. These lists are referred to as "exchange lists" because foods on the same list provide, on average, a similar number of calories and grams of carbohydrate, protein and fat. The Berkeley HeartLab "Food as Points" system divides foods into food categories and subcategories and renames them as "healthy, not-as-healthy and splurge" foods. Each food is designated a point per serving (although serving sizes do vary) and every food contained within the same list can be exchanged for another food within that list. The designation of a food to a subcategory is based on different parameters. The following list provides examples.

GRAIN & STARCH "healthy" foods are those that are good sources of soluble fiber.

VEGETABLE "healthy" foods are the most nutrient packed vegetables having three or more of Vitamin E, A, C, K or that are high in soluble fiber.

PROTEIN "healthy" designates those foods that are categorized by the food exchange system as very lean and includes salmon and soy products because of their heart-healthy properties. The "not-as-healthy" category includes meats/meat-substitutes categorized as lean and the "splurge" foods as medium to high-fat.

DAIRY nonfat and soy (again for its heart-healthy properties) products are listed as "healthy" whereas higher fat choices are in the other two categories.

FAT categories are divided relative to the type of major fatty-acid the food supplies: "healthy" are those fats that are primarily made up of monounsaturated fatty acids, or omega-3-fatty acids or that are high in isoflavones, "not-as-healthy" are fats containing mostly polyunsaturated fatty acids and "splurge" are those fats that are made up primarily of saturated fatty acids.

SWEETS categories are divided relative to simple sugar content and dietary fiber.

EXAMPLE 5

"Exercise as Points" System

Physical activity can positively influence plasma lipid and lipoprotein concentration and reduce coronary artery disease risk levels (Caso E K (1950) Journal of the American Diabetic Association 26:575–583). In summary, physical activity and weight loss have been shown to decrease VLDL, IDL, LDL, APO B, triglycerides, HDL 3, insulin, blood glucose, fibrinogen levels as well as reverse non-insulin dependent diabetes, improve LDL subclass distribution, fibrinolysis and blood pressure and increase LDL particle size, insulin sensitivity and HDL 2 concentrations (Durstine J L and Thompson P D (2001) Cardiol Clin 19:471–88; Haskell W L (1994) Med Sci Sports Exerc 26:649–660). The appropriate amount of exercise to promote these responses is dependent upon gender, age, height relative to weight, and the combined risk level of each individual (Halle M et al. (1999) Int J Sports Med 20:464–9). The appropriate duration for most activity is around 20–30 minutes but this can vary depending on the intensity of the activity. For reducing cardiovascular risk levels, it is more important that physical activity is performed on a regular basis as the short-term (acute) effects of exercise that last up to 72 hours greatly improve patients' metabolic condition. Long-term exercise training increases exercise capacity, which permits larger individual exercise sessions and a greater acute effect. The exercise goal to work towards is 20–30 minutes of continuous physical activity on most days of the week.

The Berkeley HeartLab "Exercise as Points" system quantifies how much physical activity is appropriate to reduce risk factors relative to an individual's personal set of demographic, medical, and cardiovascular risk parameters. This system assigns a point recommendation for exercise each day. This "Exercise as Points" system is based on the *Compendium of Physical Activities: an update of activity codes and MET intensities* (Durstine J L et al. (2001) Sports Med 31:1033–62). In our system, exercises associated with one point are equivalent to the intensity of exercise usually described as one MET (the ratio of work metabolic rate relative to resting metabolic rate). One MET is defined as the energy expenditure for sitting quietly, which for the average adult is approximately 3.5 mls of $O_2$ per kilogram of body weight per minute. However, we prescribe exercise in 15 minute blocks so it is not an exact correlation. But for purposes of exercise prescription by the physician all exercise listed under one point per 15 minutes of activity are activities that are equivalent to one MET (independent of time).

The purpose of our simplification of the MET as a method of exercise prescription is to make it easier for the patient to understand and use. All exercises are categorized by intensity and points; very light effort activities are those that are designated 2 or 3 points per 15 minutes and are associated with activities that are typically assigned 2 or 3 METs. We have further categorized the activities under this very light effort category as those of daily living, sports & recreation, or conditioning. The selection of the appropriate general effort (very light, light, moderate, vigorous, and very vigorous) and the further selection or exclusion of activities as defined by the subcategories (daily living, sports & recreation, and conditioning) are left up to the physician. The "Exercise as Points" system only recommends a daily exercise point goal appropriate to reduce risk factors based on the conditions of the individual patient. It is up to the clinician to assign the appropriate intensity and type of activities acceptable based on a more detailed medical knowledge of each patient's condition.

EXAMPLE 6

Berkeley HeartLab Diet & Exercise ToolKit

In order to appropriately reduce risk levels, a comprehensive approach to treatment must be followed. The Berkeley HeartLab Diet & Exercise ToolKit is to be used in combination with the Personalized Subclass Diet & Exercise Calculator or Color Wheel and the Berkeley HeartLab Treatment Guidelines. The ToolKit may be used to incorporate the results of Berkeley HeartLab advanced testing in the development of comprehensive treatment plans for patients at risk of or diagnosed with cardiovascular disease. The Treatment Guidelines should be considered in the context of the entire clinical history of the patient being treated. Other specific components of the patient's history must be considered before developing a final treatment plan.

The Berkeley HeartLab Diet & Exercise ToolKit is designed to aid the clinician in providing their patients with materials for lifestyle intervention. The actual personalized recommendations for diet and exercise are generated by the Personalized Subclass Diet & Exercise Calculator or appear on the patient's Lab Report. The ToolKit is divided into the following sections by tabs and contains master documents intended for duplication:

Moderate (35%) Fat Diet
1200 & 1600 calorie meal plans
1800 & 2000 calorie meal plans
2400 & 2800 calorie meal plans
3000 & 3600 calorie meal plans
Not-so-Low (25%) Fat Diet
1200 & 1600 calorie meal plans
1800 & 2000 calorie meal plans
2400 & 2800 calorie meal plans
3000 & 3600 calorie meal plans
Very Low (20%) Fat Diet
1200 & 1600 calorie meal plans
1800 & 2000 calorie meal plans
2400 & 2800 calorie meal plans
3000 & 3600 calorie meal plans "Food as Points"—a food list that categorizes food by health value and designates a point value to each food for meal planning.

Tables, displaying the amounts of certain vitamins and nutrients, for example, Vitamin E and beta-carotene, present in various foods.

Recipes—Berkeley HeartLab (BHL) recipes to accompany meal plans.

Daily Log—for meal planning using the "Food as Points" system and for logging activity using the "Exercise as Points" system.

Calorie Calculator—a paper calculator for determining appropriate caloric recommendations relative to body mass index (on reverse side of calorie calculator).

"Exercise as Points"—categorizes exercise by effort, sub-categorizes exercise by type of activity and designates a point value to each exercise activity. Point values are equivalent to METs (metabolic equivalents), independent of time.

EXAMPLE 7

Diet & Exercise Calculator and Recommendation

The Berkeley HeartLab Subclass Diet & Exercise Calculator is to be used with the Treatment Guidelines. The calculator may offer guidance to clinicians when making specific diet and exercise recommendations for their patients. Other patient problems (e.g., for diabetics, refer to the ToolKit Reference Booklet for dietary type recommendation) and current lifestyle habits must be considered before finalizing patient treatment plans.

The following factors are considered by the Diet & Exercise Calculator. First, the patient's age, gender, height, and body weight, are factored in. Second, the patient's LDL IIIa+IIIb level, selected from the following levels, is factored in: extreme ($\geq$45%); very high (35–44%); high (25–34%); borderline high (16–24%); normal ($\leq$15%). Third, the patient's HDL 2(b) level, selected from the following levels, is factored in: normal ($\geq$20% if male; $\geq$30% if female); borderline (11–19% if male; 21–29% if female); low ($\leq$10% if male; $\leq$20% if female). Fourth, the patient's HDL-C level, selected from the following levels, is factored in: negative risk factor (>60 mg/dL); optimal (41–60 mg/dL); low (26–40 mg/dL); very low ($\leq$25 mg/dL). Fifth, the patient's LDL-C level, selected from the following levels, is factored in: very high ($\geq$190 mg/dL); high (160–189 mg/dL); borderline high (130–159 mg/dL); near/above optimal (100–129 mg/dL); optimal (<100 mg/dL). Six, the patient's APO B level, selected from the following levels, is factored in: high ($\geq$110 mg/dL); near/above optimal (80–109 mg/dL); optimal (<80 mg/dL). Seven, the patient's glucose level, selected from the following levels, is factored in: very high (>126 mg/dL); high (110–126 mg/dL); optimal (<110 mg/dL). Eight, the patient's insulin level, selected from the following levels, is factored in: high ($\geq$12 µU/ml); normal (<12 µU/ml). Nine, the patient's triglycerides level, selected from the following levels, is factored in: extreme (>1000 mg/dL); very high (500–999 mg/dL); high (200–499 mg/dL); borderline (150–199 mg/dL); normal (<150 mg/dL). Ten, the patient's homocysteine level, selected from the following levels, is factored in: high ($\geq$14 µmol/L); borderline (10–13 µmol/L); optimal (<10 µmol/L). Eleven, the patient's Lp(a) level, selected from the following levels, is factored in: high ($\geq$20 mg/dL); optimal (<20 mg/dL). Twelve, the patient's APO E genotype, selected from the following genotypes, is factored in: 4/4 or 3/4; 3/3 or 2/4; 2/2 or 2/3.

An example of a diet and exercise recommendation, as it appears on the lab report or with use of the calculator, is as follows:

Your Personal Subclass Diet & Exercise recommendation is 2000–2400 calories (35–43 pts) from a not-so-low (25%) fat diet with only "healthy foods" and 20 pts of exercise.

According to the above recommendation, from the Diet & Exercise ToolKit the clinician should provide the patient with copies of the following:

2000 and 2400 calorie meal plans from the not-so-low (25%) fat diet section
Food as Points list
Exercise as Points list
Daily Log for meal planning and logging exercise
Recipes On the "Exercise as Points" handout, the clinician must determine the appropriate exercise intensity category for the patient, e.g.:

Light Effort Activities, 2–3 points And select subcategory activities that are appropriate for the individual patient:
Daily Living
Sport and Recreation
Conditioning All of the articles, books, patents, patent applications, and other references cited in this patent application are hereby incorporated by reference.

Although certain presently preferred embodiments of the invention have been described herein, it will be apparent to those of skill in the art to which the invention pertains that variations and modifications of the described embodiment may be made without departing from the spirit and scope of the invention. Accordingly, it is intended that the invention be limited only to the extent required by the following claims and the applicable rules of law.

The invention claimed is:

1. A method for selecting an optimal diet for a patient, comprising:
   (a) considering LDL IIIa+IIIb or HDL 2(b) subclass levels in the patient; and
   (b) selecting an optimal diet based on the LDL IIIa+IIIb or HDL 2(b) subclass level(s) considered in step (a);
   wherein the diet selected comprises a moderate (35%) fat diet when HDL 2(b) is less than or equal to 10% of HDL cholesterol if the patient is male, or when HDL 2(b) is less than or equal to 20% of MDL cholesterol if the patient is female, or when LDL IIIa+IIIb is greater than or equal to 35% of LDL-C cholesterol; and
   wherein the diet selected comprises a not-so-low (25%) fat diet when LDL IIIa+IIIb is less than 35% of LDL-C cholesterol.

2. The method according to claim 1, wherein the LDL IIIa+IIIb or HDL 2(b) subclass level considered is expressed in quantitative terms.

3. The method according to claim 1, wherein the LDL IIIa+IIIb or HDL 2(b) subclass level considered is expressed in terms of mg/dL.

4. A method for treating a patient, comprising:
   (a) selecting an optimal diet according to the method of claim 1;
   (b) prescribing the optimal diet selected in step (a) to the patient; and
   (c) monitoring LDL IIIa+IIIb or HDL 2(b) subclass levels in the patient.

* * * * *